US009995746B2

(12) United States Patent
Abshire et al.

(10) Patent No.: US 9,995,746 B2
(45) Date of Patent: Jun. 12, 2018

(54) RAPID DUAL DIRECT FLUORESCENT ANTIBODY ASSAY FOR THE IDENTIFICATION OF *BACILLUS ANTRHACIS*

(71) Applicant: The United States of America as represented by the Secretary of the Army, Washington, DC (US)

(72) Inventors: Teresa Abshire, Frederick, MD (US); Wilson J Ribot, Hanover, PA (US)

(73) Assignee: The United States of America, as represented by the Secretary of the Army, Washington, DC (US)

( * ) Notice: Subject to any disclaimer, the term of this patent is extended or adjusted under 35 U.S.C. 154(b) by 0 days. days.

(21) Appl. No.: 15/125,910

(22) PCT Filed: Apr. 2, 2014

(86) PCT No.: PCT/US2014/032633

§ 371 (c)(1),
(2) Date: Sep. 13, 2016

(87) PCT Pub. No.: WO2015/152908

PCT Pub. Date: Oct. 8, 2015

(65) Prior Publication Data

US 2017/0003287 A1 Jan. 5, 2017

(51) Int. Cl.

| | |
|---|---|
| *A61K 38/00* | (2006.01) |
| *G01N 33/569* | (2006.01) |
| *C07K 16/12* | (2006.01) |
| *C07K 16/44* | (2006.01) |

(52) U.S. Cl.

CPC .... *G01N 33/56911* (2013.01); *C07K 16/1278* (2013.01); *C07K 16/44* (2013.01); *C07K 2317/52* (2013.01); *C07K 2317/55* (2013.01); *C07K 2317/70* (2013.01); *G01N 2333/32* (2013.01); *G01N 2469/10* (2013.01)

(58) Field of Classification Search

None

See application file for complete search history.

(56) References Cited

U.S. PATENT DOCUMENTS

| | | | |
|---|---|---|---|
| 4,816,567 | A | 3/1989 | Cabilly |
| 5,591,828 | A | 1/1997 | Bosslet |
| 6,448,018 | B1 | 9/2002 | Nakayama |
| 2010/0330074 | A1 | 12/2010 | Kubler-Kielb |

FOREIGN PATENT DOCUMENTS

| | | |
|---|---|---|
| EP | 404097 | 12/1990 |
| WO | WO 1993/08829 | 5/1993 |
| WO | WO 1993/11161 | 6/1993 |
| WO | WO 96/27011 | 9/1993 |

OTHER PUBLICATIONS

Ezzell et al , Infection and Immunity , vol. 56, No. 2, p. 349-356 Feb. 1988.*

Ezzel et al.,1990, J. Clin. Microbial 28, 223-231.

De, B.K. etal., Emerg. Infect. Dis. 2002, 8:1060-65.

Tatti et al., Appl. Immunohistochem Mol Morphol., Jun. 1, 2006, vol. 14, No. 2, pp. 234-243.

Ezzell et al., Salisbury Medical Bulletin, 1996, Special Supplement, No. 87, p. 42.

PCT International Search Report dated Aug. 27, 2014 in parallel PCT application PCT/US2014/032633 (filed Apr. 2, 2014)(2 pages).

PCT International Preliminary Report on Patentability dated Aug. 27, 2014 in parallel PCT application PCT/US2014/032633 (filed Apr. 2, 2014)(6 pages).

* cited by examiner

*Primary Examiner* — Ja'Na Hines
*Assistant Examiner* — Khatol Shahnan Shah
(74) *Attorney, Agent, or Firm* — Nash and Titus, LLC

(57) ABSTRACT

In this application is described a method for rapidly and accurately identifying *B. anthracis* in a sample by simultaneously detecting the presence of cell wall antigen and capsule antigen in the same sample culture grown under capsule inducing conditions. Other uses and advantages of the method of the invention are described herein.

16 Claims, 2 Drawing Sheets

From overnight 5% SBA culture under atmospheric $CO_2$

Original assay　　　　　　　　　　Tandem Assay

Suspension of cells from overnight culture:　　Suspension of cells from overnight culture:

1) A. Inoculation of resuspended cells into capsule inducing liquid broth medium. Incubate x 2-4 hrs.

1) Inoculation of resuspended cells onto 5% SBA; Incubate 2-2.5 hrs under 20% $CO_2$

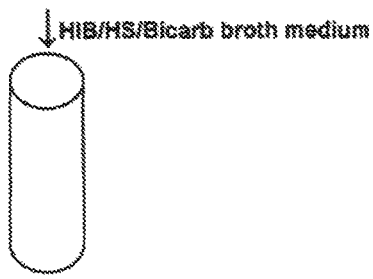

↓ HIB/HS/Bicarb broth medium

B. Stain resuspended cells for pCHO with anti-pCHO MAb (FITC tagged: green signal).

2) Stain resuspended cells and pCHO using anti-pCHO FAb (ATTO 594 tagged: red signal) and anti-capsule MAb (FITC tagged: green signal) in same reaction tube.
Observe simultaneously stained cells 2) Post 2-4 hrs. culturing, stain cells from broth medium for capsule using Anti-capsule MAb (FITC tagged: green signal).

Figure 1

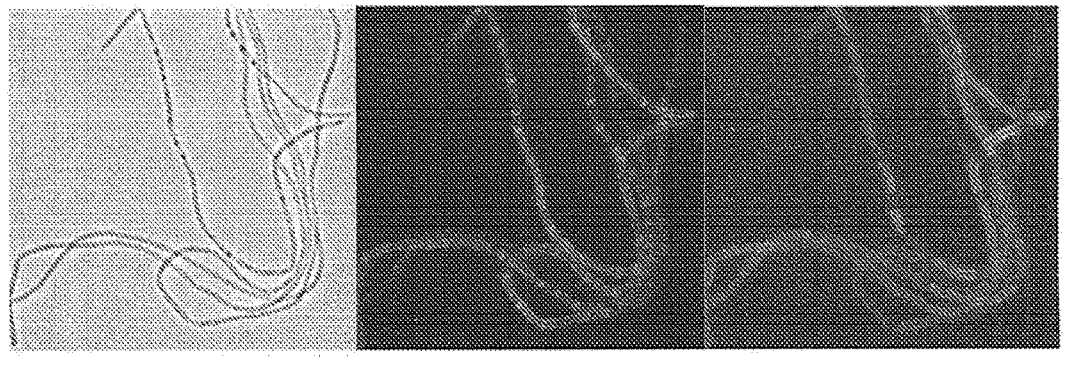
Set A: bright field    cell wall    capsule
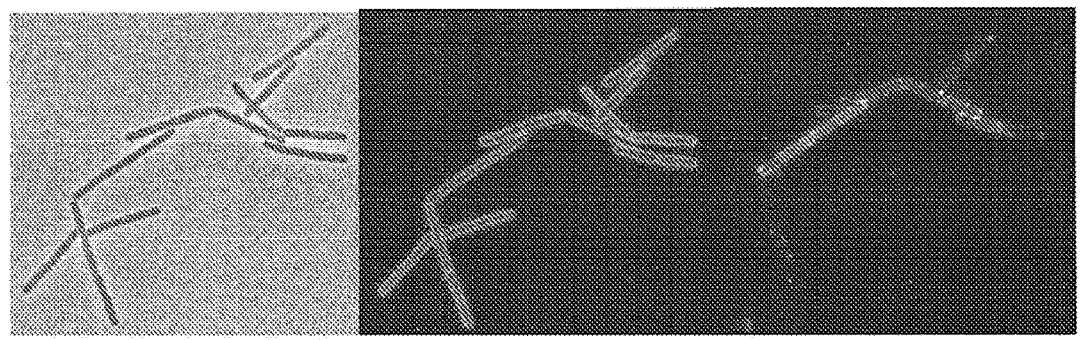
Set B: bright field    cell wall    capsule
Figure 2

RAPID DUAL DIRECT FLUORESCENT ANTIBODY ASSAY FOR THE IDENTIFICATION OF *BACILLUS ANTRHACIS*

INTRODUCTION

The direct fluorescent antibody assay (DFA) is a procedure that uses antibodies tagged with fluorescent dyes to detect the presence of specific antigens on the surface of a cell or microorganism. Recognized antigens are visible when examined microscopically using a light source which causes the antibody-bound fluorophore to emit a specific wavelength.

A two-component DFA assay, using fluoroscein-labeled monoclonal antibodies specific to the *Bacillus anthracis* galactose-N-acetylglucosamine polysaccharide (Gal-NAG-PS) in the cell wall and poly-D-glutamic acid (CAP) capsule antigen is currently available for detection of *Bacillus anthracis* in a sample. Although other *Bacillus* species produce poly-D-glutamic acid capsular material (i.e. certain *B. subtilis* and *B. licheniformis* strains), and two *B. cereus* strains produce the galactose-N-acetylglucosamine polysaccharide (Ezzel et al., 1990, J. Clin. Microbiol 28, 223-231), the combination of both traits is strongly indicative of *B. anthracis*.

The current method requires that the test sample is incubated under two different growth conditions: one which greatly reduces capsule formation of *B. anthracis* (on sheep agar, at 35-37° C., under atmospheric CO2 conditions for 16-24 hours), and one allowing capsule formation (20% CO2 supplement is frequently used). This is necessary due to the observation that the anti-Gal-NAG-PS monoclonal antibody is inhibited from reacting with the cell wall when the capsule is present. Consequently, each antigen in the DFA assay is detected in a separate vial, each vial containing a different subculture of the sample. The necessity for different culture conditions of the sample and separate immunoassay vials for each antigen increases the time and cost required to complete the assay, and allows for misinterpretation of results.

What is needed is a more efficient and less cumbersome method which allows the detection of both *B. anthracis* antigens in one vial or culture. Eliminating the need for multiple culture conditions increases the rapidity and accuracy of *B. anthracis* identification. The present invention addresses this and other unfulfilled needs in the art.

SUMMARY OF THE INVENTION

In this application is disclosed a novel and rapid detection method for simultaneously detecting two of the identifying indicators of *Bacillus anthracis*, the cell wall polysaccharide Gal-NAG-PS and the capsule poly-D-glutamic acid.

In order to design an assay for detection of both components, the inventors needed to understand why the Gal-NAG-PS monoclonal did not stain the cell wall in the presence of the capsule. Characterization of the *B. anthracis* capsule using fluorescent dextran beads of varying molecular weights revealed that the capsule polypeptides assembled into a molecular sieve with decreasing density as the distance from the cell wall increased. The inventors determined that dextran beads with stokes radii approximating those of full size immunoglobulin's (IgG and IgM) were unable to penetrate through the capsule layers to reach the cell wall. Conversely, by fluorescently labeling the 5.16 kDa antimicrobial peptide HBD-3, the inventors determined that this small peptide was able to penetrate through the capsule layers to bind the cell wall. These results provided one explanation for the inability to detect protein molecules binding to, or present on, the bacterial cell wall using complete IgG or IgM antibodies.

To investigate the possibility that a smaller antibody molecule may able to penetrate the capsule, the inventors fragmented the anti-Gal-NAG-PS monoclonal antibody (IGM type, 900 KDa) to produce Fab fragments (50 KDa) and tested if the Fab fragment can penetrate the capsule layer, and react with its antigen in the cell wall. Surprisingly, the Fab fragment was able to permeate through the capsule and bind to the cell wall antigen even in the presence of bound anti-CAP antibody.

Therefore, the present invention provides a method for identifying the presence of *Bacillus anthracis* in a sample by simultaneously identifying the presence of capsule and cell wall in one sample. The method encompasses the addition of detectably labeled antibody Fab fragment specific for a cell wall antigen in tandem with differentially detectably labeled anti-capsule antibody, in a microbial culture from a biological, environmental, or forensic sample, and detecting the presence of complexes formed such that presence of label specific for the anti-cell wall Fab indicates cell wall, and presence of label specific for anti-capsule antibody indicates capsule, and presence of both labels strongly indicates the presence of *B. anthracis* in the sample. In a specific embodiment, the cell wall Fab antibody is anti-Gal-NAG-PS. In another specific embodiment, the capsule antibody is anti-poly-D-glutamic acid.

The present invention provides several advantages. In the present invention, a single incubation under capsule inducing conditions can be used for detecting both the *B. anthracis* cell wall antigen and capsule antigen, eliminating the need for additional subcultures at varying conditions. Staining the same *bacillus* with antibodies conjugated with different labels, e.g. contrasting fluorophores, confers accuracy and minimizes misinterpretation of results. In addition, the present invention allows the identification of some atypical isolates of *B. anthracis* which produce capsule under atmospheric CO2 conditions, as well as aberrant *Bacillus* such as the pathogenic *B. cereus* that do not produce the anthracis poly-D-glutamic acid capsule, but do contain the anthracis-like cell wall polysaccharide. Previously, use of the Gal-NAG-PS IgM would not detect the cell wall, however, the anti-Gal-NAG-PS Fab antibody of the present invention would overcome this limitation.

Another major advantage of the herein described tandem DFA protocol is that it encourages the immediate analysis of any incoming culture or blood sample, without further culturing. Much information can be gathered with a first look at the sample: if it contains *B. anthracis*, the cell wall will be detected and the sample will be pCHO positive. pCHO is *B. anthracis* plasmid encoding the synthesis of cell wall N-acetyl-D-glucosamine, Gal-NAG polysaccharide. If it contains capsule, the sample will be pXO2 positive, and the capsule laden cells will be detected. pXO2 is a *B. anthracis* plasmid encoding the synthesis of poly-D-glutamyl capsule. This is a quantum leap for early identification and/or verification of *B. anthracis* in a sample. Further confirmation would follow about 3 hours later post incubation under capsule producing conditions.

Therefore, it is one object of the present invention to provide a method for identifying the presence of *Bacillus anthracis* in a sample by simultaneously identifying the presence of capsule and cell wall, by addition of detectably labeled anti-Gal-NAG-PS Fab fragment in tandem with differentially detectably labeled anti-CAP antibody, to the biological sample, microbial culture or environmental sample, and detecting the presence of complexes formed such that presence of anti-Gal-NAG-PS label indicates cell wall and presence of anti-capsule (anti-CAP) label indicates capsule and presence of both labels strongly indicates the presence of *B. anthracis* in the sample.

It is another object of the invention to provide novel test kits for detection of *B. anthracis* comprising antibodies according to the present invention. The antibodies are directly or indirectly attached to a suitable reporter molecule, e.g., an enzyme, a radionuclide, or a fluorophore. The test kit includes a container holding one or more antibodies according to the present invention and instructions for using the antibodies for the purpose of detecting *B. anthracis* in a sample by detecting the formation of the immunological complex(es) such that presence or absence of the immunological complex(es) correlates with presence or absence of *B. anthracis*.

It is still another object of the present invention to provide a method for targeting therapeutic compounds to *Bacillus anthracis*. The anti-Gal-NAG-PS and anti-CAP antibodies of the present invention can be complexed to therapeutic compounds, e.g. one or more bactericidal compound or toxin, such that the compounds are delivered to the cell wall or capsule upon contact with *Bacillus anthracis*. Some examples of compounds include 2-epimerase enzymes, e.g. 2-epimerase (Schuch et al., 2013, In Aziz, Ramy K. PLoS ONE 8(4):e60754; Vellosos et al, 2008, EMBO Rep 9: 199-205) and phage endolysines e.g. PlyG, or active portions thereof (Ganguly et al., 2013 Glycobiology 23, 820-32).

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

These and other features, aspects, and advantages of the present invention will become better understood with reference to the following description and appended claims, and accompanying drawings where:

FIG. 1. Schematic for the Original vs Tandem DFA assay. The original method required an overnight SBA culture under atmospheric CO2. From that culture the pCHO DFA could be directly performed. However, it was then necessary to create a $2^{nd}$ culture from this overnight in a capsule inducing broth medium for about 4 hours. The tandem assay of the present invention requires only one growth condition in one tube, and one slide for simultaneous observation of capsule and cell wall staining.

FIG. 2. Representative results using the tandem DFA assay of the present invention showing *B. anthracis* detected in sample under capsule inducing conditions using bright field microscopy and fluorescence detection (cell wall and capsule). Set A: represents potential staining pattern of wild type virulent strains, i.e. *B. anthracis* Sterne. Set B: represents potential staining pattern of pXO1$^-$, pXO2$^+$ strains, i.e. Pasteur controls.

DETAILED DESCRIPTION

In the description that follows, a number of terms are extensively utilized. In order to provide a clearer and consistent understanding of the specification and claims, including the scope to be given such terms, the following definitions are provided.

As used herein, the term "antigen" is a molecule capable of being bound by an antibody. Thus, antigenic determinants or epitopes are those parts of an antigen that are recognized by antibodies. An antigenic determinant need not be a contiguous sequence or segment of protein and may include various sequences that are not immediately adjacent to one another.

As used herein the terms "specific to" or "specific for" a target sequence, in relation to an antibody, relate to an antibody or antibody fragment that binds an antigen, under conditions used in given circumstances (e.g., temperature, salt concentration, etc.), but does not significantly bind to other antigens or polypeptides that are not target antigens.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

It also is specifically understood that any numerical value recited herein includes all values from the lower value to the upper value, i.e., all possible combinations of numerical values between the lowest value and the highest value enumerated are to be considered to be expressly stated in this application. For example, if a range is stated as 1% to 50%, it is intended that values such as 2% to 40%, 10% to 30%, or 1% to 3%, etc., are expressly enumerated in this specification.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (Zapata et al., 1995, Protein Eng. 8(10): 1057-1062); single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')$_2$ fragment that has two antigen-combining sites and is still capable of cross-linking antigen.

"Fv" is the minimum antibody fragment which contains a complete antigen-recognition and antigen binding site. This region consists of a dimer of one heavy-chain and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2.

"Single-chain Fv" or "sFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444-6448 (1993).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An antibody that "specifically binds to" or is "specific for" a particular polypeptide or polysaccharide or an epitope on a particular polypeptide or polysaccharide is one that binds to that particular polypeptide or polysaccharide or epitope on a particular polypeptide or polysaccharide without substantially binding to any other polypeptide or polypeptide epitope.

The word "label" when used herein refers to a detectable compound or composition which is conjugated directly or indirectly to the antibody so as to generate a "labeled" antibody. The label may be detectable by itself (e.g. radioisotope labels or fluorescent labels) or, in the case of an enzymatic label, may catalyze chemical alteration of a substrate compound or composition which is detectable.

The word "subject" includes human, animal, avian, e.g., horse, donkey, pig, mouse, hamster, monkey, chicken, sheep, cattle, goat, buffalo, and any other subject suspected of being infected with *B. anthracis*.

The language "biological sample" is intended to include biological material, e.g. cells, blood, tissues, biological fluid, or a solution for administering to a subject, such as a vaccine, or immunoglobulin. By "environmental sample" is meant a sample such as soil and water. Food samples include canned goods, meats, milk, and other suspected contaminated food. Forensic sample includes any sample from a suspected terrorist attack suspected of having anthrax, including paper, powder, envelope, container, hair, fibers, and others.

Polyclonal Antibodies. The antibodies of the present invention may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the polypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

Monoclonal Antibodies. The antibodies may, alternatively, comprise monoclonal antibodies. Monoclonal antibodies may be prepared using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the polypeptide or polysaccharide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, Academic Press, (1986) pp. 59-103). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies (Kozbor, 1984, J. Immunol., 133:3001; Brodeur et al., Monoclonal Antibody Production Techniques and Applications, Marcel Dekker, Inc., New York, (1987) pp. 51-63).

The culture medium in which the hybridoma cells are cultured can then be assayed for the presence of monoclonal antibodies directed against the desired antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, 1980, Anal. Biochem., 107:220.

After the desired hybridoma cells are identified, the clones may be subcloned by limiting dilution procedures and grown by standard methods (Goding, supra). Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

Bispecific antibodies are monoclonal, preferably human or humanized, antibodies that have binding specificities for at least two different antigens. In the present case, one of the binding specificities is for the *B. anthracis* antigen, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, 1983, Nature, 305:537-539). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., 1991, EMBO J., 10:3655-3659.

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., 1986, Methods in Enzymology, 121:210.

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. F(ab')$_2$ bispecific antibodies). Techniques for generating bispecific antibodies from antibody fragments have been described in the literature. For example, bispecific antibodies can be prepared can be prepared using chemical linkage. Brennan et al., 1985, Science 229:81 describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Fab' fragments may be directly recovered from E. coli and chemically coupled to form bispecific antibodies. Shalaby et al., 1992, J. Exp. Med. 175:217-225 describe the production of a fully humanized bispecific antibody F(ab')$_2$ molecule. Each Fab' fragment was separately secreted from E. coli and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., 1992, J. Immunol. 148(5):1547-1553. The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., 1993, Proc. Natl. Acad. Sci. USA 90:6444-6448 has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_h$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., 1994, J. Immunol. 152:5368.

Antibodies with more than two valencies are contemplated. For example, trispecific antibodies can be prepared. Tutt et al., 1991, J. Immunol. 147:60.

Exemplary bispecific antibodies may bind to two different epitopes on a given B. anthracis antigen herein. Alternatively, an anti-B. anthracis antigen arm may be combined with an arm which binds to a triggering molecule on a leukocyte such as a T-cell receptor molecule (e.g. CD2, CD3, CD28, or B7), or Fc receptors for IgG (FcγR), such as FcγRI (CD64), FcγRII (CD32) and FcγRIII (CD16) so as to focus cellular defense mechanisms to the bacilli. Bispecific antibodies may also be used to localize cytotoxic agents to B. anthracis bacilli, or other bacilli with CAP or Gal-NAG-PS. For example, these antibodies possess a cell wall binding arm and an arm which binds a cytotoxic agent or a bactericidal agent, for example, epimerox or PlyG.

The invention also pertains to immunoconjugates comprising an antibody conjugated to a bactericidal agent such as an antibiotic or an enzyme which is able to digest part or all of the cell wall, for example, Epimerox or PlyG.

Conjugates of the antibody and bactericidal agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as his (p-azidobenzoyl) hexanediamine), bis-diazonium derivatives (such as bis-(p-diazoniumbenzoyl)-ethylenediamine), diisocyanates (such as tolyene 2,6-diisocyanate), and his-active fluorine compounds (such as 1,5-difluoro-2,4-dinitrobenzene).

The present invention pertains to a method for detecting B. anthracis in a sample suspected of containing Bacillus anthracis. The method includes culturing the sample under capsule inducing conditions. Capsule-inducing conditions are well known to people in the art, see Examples below. After culturing, the sample is contacted simultaneously with two antibodies, one Fab antibody specific for cell wall and one antibody specific for the capsule, allowing the antibody to bind to its antigen to form an immunological complex, detecting the formation of the immunological complex of each antibody, and correlating the presence of each immunological complex with the presence of B. anthracis in the sample. The sample can be biological, environmental, forensic, or a food sample.

Two monoclonal antibodies are described herein. The development and characterization of the monoclonal antibody to B. anthracis cell wall galactose-N-acetylglucosamine polysaccharide, also known as EAII-6G6, was described by Ezzell et al., 1990, Journal of Clinical, Microbiology, volume 28, pages 223-231. Briefly, guanidine extracts of crude Bacillus anthracis cell wall were used to vaccinate BALB/c mice and to develop monoclonal antibody to vegetative cell surface antigens. Two Hybridomas were selected which produced immunoglobulin M immunoglobulin's, directed to an epitope associated with the galactose-N-acetyl-D-glucosamine polysaccharide. Both demonstrated specificity in their binding to purified B. anthracis cell wall, o-stearoyl-polysaccharide conjugates, and intact nonencapsulated vegetative cells. Electron microscopy showed that both monoclonal antibodies interacted with the cell wall of vegetative cells as well as with the cortex of spores. Neither monoclonal reacted with encapsulated vegetative cells nor with intact spores. After conjugation to fluorescein isothiocyanate, the monoclonals stained intensely all B. anthracis strains tested, some strains of Bacillus cereus, but non of the 20 other Bacillus spp.

The original form, whole IgM, of the antibody has been used for about 20 years by the Department of Defense. In the present invention, a Fab fragment of the anti-Gal-NAG-PS cell wall IgM was used as described in the Examples below. Methods for production of Fab fragments from whole antibody molecules is known in the art. The anti-Gal-NAG-PS cell wall IgM was digested into Fab fragments and subsequently labeled.

Methods for making monoclonal antibodies to the poly-D-glutamic acid (PDGA) polypeptide are known in the art. See for example Kozel et al., 2007, Infect. Immun. 75, 152-163 or Kozel et al., 2004, PNAS 101, 5042-5047. The monoclonal antibodies used in the herein described invention FDF-1B9 (De, B. K. et al., Emerg. Infect. Dis. 2002, 8:1060-65), can potentially be replaced with another PDGA monoclonal known to bind capsule. The substituted monoclonal antibody should be able to bind the PDGA and not interfere with binding of the cell wall monoclonal antibody.

Similarly, other monoclonal antibodies which specifically bind the cell wall galactos-N-acetylglucosamine polysaccharide can be used. Characteristics of such a monoclonal and methods of preparing same are found in Ezzell, et al., 1990, J. Clin. Microbiol. 28, 223-231.

The antibodies used in the diagnostic assays described herein can be labeled with a detectable moiety. The detectable moiety should be capable of producing, either directly or indirectly, a detectable signal. For example, the detectable moiety may be a fluorescent or chemiluminescent compound, such as fluorescein isothiocyanate, rhodamine, or luciferin, auramine, TEXAS RED (sulforhodamine 101 acid chloride), AMCA blue, or an enzyme, such as alkaline phosphatase, beta-galactosidase or horseradish peroxidase. Any method known in the art for conjugating the antibody to the detectable moiety may be employed, including those methods described by Hunter et al., 1962, Nature, 144:945; David et al., 1974, Biochemistry, 13: 1014; Pain et al., 1981, J. Immunol. Meth., 40:219; and Nygren, 1982, J. Histochem. and Cytochem., 30:407. Labels include, but are not limited to moieties that are directly or indirectly detectable such as radioactive elements, enzymes, fluorescent molecules or chemicals, and others. In one embodiment, the Fab fragment is labeled with a fluorophore, specifically, Dylight 594, as described in the Examples. Other labels can be used as is known to people with skill in the art.

The present invention also provides kits which are useful for carrying out the present invention. The present kits comprise a first container means containing the above-described antibodies. The kit also comprises other container means containing solutions necessary or convenient for carrying out the invention. The container means can be made of glass, plastic or foil and can be a vial, bottle, pouch, tube, bag, etc. The kit may also contain written information, such as procedures for carrying out the present invention or analytical information, such as the amount of reagent contained in the first container means. The container means may be in another container means, e.g. a box or a bag, along with the written information.

The following examples are included to demonstrate preferred embodiments of the invention. It should be appreciated by those of skill in the art that the techniques disclosed in the examples which follow represent techniques discovered by the inventors and thought to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

All documents cited herein are hereby incorporated in their entirety by reference thereto.

Example 1

Molecular Architecture of *B. anthracis* Capsule

Methods

Encapsulated *B. anthracis* bacilli (Ames strain), or the unencapsulated Ames CapA derivative were incubated with FITC labeled dextrans (green) (FDx, Molecular Probes, Life Technologies, Frederick, Md.) for 30 minutes at room temperature. Bacterial DNA was then stained with DAPI (blue). Images were acquired using a TE2000 microscope equipped with phase contrast and fluorescence filters. Images were overlaid and the pixel intensity of FDx fluorescence was determined across the center of the cells using In-Vivo Imaging software (Media Cybernetics, Rockville, Md.). Fab antibodies were prepared from anti-capsule monoclonal antibody FDF-1B9 (USAMRIID) using a commercially available kit. Products were characterized by size exclusion chromatography using an FPLC system and a Superose 6 SEC column (Amersham Pharmacia, Piscataway, N.J.), in PBS with monitoring at 280 nm. Anti-capsule IgM was labeled with FITC (green fluorescence), and anti-capsule Fab was labeled with ALEXAFLUOR (carboxamido-(6-azidohexanyl, triethylammonium salt) (hereafter referred to as AF594) (red fluorescence).

Results

The results showed that 3 kDa and 500 kDa FDx were not impeded from reaching the poly-D-gamma-glutamic acid of an unencapsulated strain (CapA, figure not shown). In contrast, when using the encapsulated Ames strain, the line intensity profiles revealed that the peaks of FDx fluorescence were further from the cell wall for the 40 kDa and 500 kDa FDx than for the 3 kDa FDx. These results suggested that FDx of increasing molecular size were blocked from reaching the cell walls of encapsulated bacilli by PGGA.

In previous studies, we determined that intact antibodies, (IgG and IgM), were not able to completely penetrate the capsule to recognize antigens on the cell wall. Considering the results obtained of the FDx experiment, we predicted that IgG antibody having a Stokes radius of 5.5 nm, which is larger than the excluded 40 kDa FDx, would have limited access to the bacillus cell wall. In contrast, an antibody Fab fragment with a Stokes radius of 3.2 nm closely approximates that of a 10 kDa FDx (2.8 nm), and should therefore have better access to the interior of cell wall than an intact IgG or IgM antibody.

We generated Fab fragments from anti-capsule mAb FDF-1B9 (USAMRIID, Frederick, Md.). A limited digestion resulted in 2 major peaks as determined by size exclusion chromatography (figure not shown). Peak 1 corresponded to the predicted size of IgM, and peak 2 to the predicted size of Fab fragments. In order to determine if anti-capsule IgM or Fab fragment antibodies bind to distinct regions of the capsule, we incubated encapsulated bacilli with intact FITC labeled anti-capsule mAb (IgM), and measured the pixel intensities of a line drawn through the center of the bacillus (figure not shown). We next incubated a separate aliquot of the same bacilli with AF594 labeled Fab and performed the same analysis (figure not shown). Results of the binding of IgM compared to Fab showed marked differences. The fluorescence peaks representing the maximum pixel intensities of IgM FITC binding were significantly farther away from the bacilli than the peaks for Fab binding (figure not shown).

As predicted, these results suggested that the anti-capsule IgM was binding poly-D-gamma-glutamic acid (PGGA) exterior to the anti-capsule Fab. In order to verify that this was the case, we incubated encapsulated bacilli with AF594 labeled Fab for 15 minutes first, washed away unbound antibody, then incubated the bacilli with FITC labeled IgM for 15 minutes (figure not shown). Images were captured and a fluorescence intensity profile was generated by drawing a line across the bacillus and graphing the pixel intensities. The analysis revealed that the FITC labeled IgM was deposited on the surface of the PGGA capsule, and farther away from the cell wall than the binding of AF594 Fab. In addition, incubation with FITC IgM after incubation with AF594 Fab changed the staining pattern for AF594 Fab from a sharp rim pattern (figure not shown) to a diffuse pattern with no clear zone between the AF594 Fab signal and the cell wall. These results suggested that while anti-capsule IgM binds to the exterior of the capsule, it also changes the structure of the interior layers of the capsule.

Conclusions

The *B. anthracis* poly-D-glutamic acid capsule functions as a molecular sieve. The capsule has a variable porosity that increases with distance from the cell wall. A high density of the polypeptide at the capsule interior prevents penetration of large macromolecules to sites near the cell wall. In contrast, the capsular edge consists of capsular polypeptide in a lower density that exhibits increased permeability to macromolecules. Macromolecules having Stokes radii of greater than, or equal to 4.6 nm (i.e. IgG and IgM) are impeded from reaching the *B. anthracis* bacillus cell wall by the PGGA capsule. Fragmentation of antibodies into Fab fragments facilitates the penetration of antibodies through the PGGA capsule to reach the bacillus cell wall.

Example 2

Tandem DFA Assay
Materials and Equipment
5% sheep blood agar (SBA) plates
PBS (sterile)
Fluoromount G (or equivalent quench/mountant)
Anti-*B. anthracis* pCHO FAb Dylight 594 DFA reagent
Anti-*B. anthracis* capsule IgM FITC DFA reagent
Incubator (equipped for 20% $CO_2$ supplementation), 35-37° C.
*B. anthracis* Pasteur (positive control: spores or vegetative cells)
*B. cereus* NCTC 2599 or equivalent (negative control: spores or vegetative cells)
Test sample(s)
Epifluorescent microscope equipped with filters (EF 4 TEXAS RED (sulforhodomine 101 acid chloride) HyQ or equivalent for Dylight 594; B-2 E/C or equivalent for FITC)
Bleach rite (or equivalent NA Hypochlorite disinfectant)
Procedure
"Quick Look" Assay
Note: It is highly recommended to perform a STAT tandem DFA on the incoming sample when presented in a vegetative cell form. Early detection of target antigens will expedite results. A positive pCHO result is indicative of *Bacillus anthracis*; it is very possible that sufficient capsule is present for a positive DFA result. Continue the incubation as per the procedure, but initial results should be reported.
Criteria to consider for determining potential 'quick look' DFA:
1) Organisms in sample must be in vegetative cell form
2) Must be less than 24 hours old
3) Must have sufficient vegetative cells available a. Ideally presented on 5% SBA perform quick morphologic examination
   i. Non-hemolytic
   ii. Ground glass in appearance
   iii. Sufficient vegetative cells can be tested from individual colony (ies).
b. If presented in broth form
   i. Microscopic examination of wet mount revealing bacillus possibly single to multiple cells/chain
   ii. Positive Gram stain
   iii. Purity of wet mount examination of sample (are other bacteria present)
   iv. Depending on number of cells per field of view and other non-*bacillus anthracis* cells present may need to concentrate cells so low frequency of *B. anthracis* cells are not 'missed'. If cell concentration is too low, cells may be pelleted via centrifugation and resuspended in 5 µl of residual liquid at end of assay.

On Slant with No Isolated Colonies:

Remove 1 µl loopful of culture material, transfer to 100 µl of sterile PBS and resuspend well. (Resuspended Material Here could be used for "quick look" then proceed to remainder of DFA procedure).

On 5% SBA or Other Medium Type with Isolated Colonies:

Remove 1 µl loopful of isolated colony culture material (or entire colony if insufficient material to fill loop) and transfer to 100 µl of sterile PBS; this constitutes the inoculum. Resuspend the inoculum well. (Resuspended Material Here could be used for "quick look" then proceed to remainder of DFA procedure).

Tandem DFA for "Quick Look"—

Transfer 10 µl of the inoculum from above to a 250-500 µl eppendorf tube. Repeat for each inoculum and controls (NOTE: cannot perform STAT DFA on spores, only vegetative cells). Perform DFA assay as noted below.

In separate tubes, dilute 5 µl of each test and control cells with 5 µl of PBS. To each tube, add 2.5 µl of the pCHO FAb Dylight 594 DFA reagent and mix with pipet tip. Allow to sit for approximately 5 minutes at room temperature and then to each tube, add 2.5 µl of the capsule IgM FITC DFA reagent and repeat mixing with pipet tip. This constitutes the DFA reaction tube. Continue to incubate at room temperature (or at 35-37° C.) for an additional 5-10 minutes.

Post-incubation, add 20 µl of PBS to the DFA reaction tube and mix with pipet tip to 'wash'.

To clean tube, place approximately 2 µl of Fluorogel quench, then immediately transfer approximately 1 µl of DFA reaction tube and mix well with pipet tip. Note: the quench to reaction tube ratio should be 2:1; adjust volumes accordingly. Transfer approximately 2 µl of the quench/DFA reaction material to microscope slide and add cover slip.

Examine cells using epifluorescent microscopy equipped with appropriate filters (EF 4 TEXAS RED (sulforhodomine 101 acid chloride) HyQ or equivalent for viewing Dylight 594 conjugated anti-pCHO FAb; B-2E/C or equivalent for FITC conjugated anti-capsule IgM)

Regular DFA Assay

Incoming sample(s):

As Spores: Unknown purity of sample dictates that material be plated onto 5% SBA, streaked for isolation and cultured for 18-24 hrs @ 35-37° C. under supplemented 20% CO2 prior to DFA procedure. At this time, *B. anthracis* Pasteur and *B. cereus* NCTC 2599 controls should also be plated (from spore form if available).

As environmental sample in liquid form: Plate 50 μl of liquid onto 5% SBA and streak for isolation. Incubate at 35-37° C. for 18-24 hrs.

From slant with no isolated colonies: Remove 1 μl loopful of culture material, and streak for isolation on 5% SBA. Incubate at 35-37° C. for 18-24 hrs.

On 5% SBA or other medium type with isolated colonies: Remove 1 μl loopful of isolated colony culture material (or entire colony if insufficient material to fill loop) and streak for isolation on fresh 5% SBA. Repeat on several suspect colonies. Incubate at 35-37° C. for 18-24 hrs.

Controls: *B. anthracis* Pasteur and *B. cereus* NCTC 2599: Plate 1 μl of stock spore suspension (*B. anthracis* Pasteur and *B. cereus* NCTC 2599 stocks $10^7$ to $10^9$ spore/ml) onto SBA plate and streak for isolation. Incubate all cultures at 35-37° C. for 18-24 hrs.

Tandem DFA

Inspect colony formations on 18-24 hr 5% SBA cultures. Suspect colonies should mimic the general characteristics of *B. anthracis* such as, but not to be restricted to, colonies exhibiting non-hemolytic, raised, 3-6 mm diameter, round to slight oblong shape, grayish white to tannish color, ground glass appearance with possible Medusa head formations.

From 18-24 hr 5% SBA cultures, remove 1 μl loopful of isolated suspect colony culture material (or entire colony if insufficient material is available to fill loop) and transfer to 100 μl of sterile PBS; this constitutes the inoculum). Resuspend the inoculum via gentle vortexing or mixing with uptake and release of suspension with pipet.

Transfer 50 μl of the inoculum to surface of 5% SBA plate. Using end of inoculation loop (or disposable spreader), spread liquid in lawn fashion over ⅓ to ½ of surface area until absorbed into agar. Repeat steps with several isolated colonies on separate 5% SBA plates. Repeat steps with 2 colony representatives from each control plate. Incubate all plates at 35-37° C. under 20% supplemented $CO_2$ for 2-2.5 hours (2.5 hrs maximum).

Post 2-2.5 hr incubation of cultures, apply 100 μl of sterile PBS onto surface of agar where 'frosty' appearance of growth is visible. Using inoculating loop, scrape off growth within a quarter size area, then tilt plate to retrieve the vegetative cell rich suspension; this constitutes the test cells. Transfer suspension to clean labeled eppendorf tube; hold on ice if cannot perform DFA immediately. Repeat for each sample and control culture.

In separate tubes, dilute 5 μl of each test and control cells with 5 μl of PBS. To each tube, add 2.5 μl of neat anti-*B. anthracis* pCHO FAb Dylight 594 DFA reagent and mix with pipet tip. Allow to sit for approximately 5 minutes at room temperature and then to each tube, add 2.5 μl of the anti-*B. anthracis* capsule IgM FITC DFA reagent and repeat mixing with pipet tip. This constitutes the DFA reaction tube. Continue to incubate at room temperature for an additional 5-10 minutes. Alternatively, tubes can also be incubated at 35-37° C. for 5-10 minutes.

Post-incubation, add 20 μl of PBS to the DFA reaction tube and mix with pipet tip to wash.

To clean tube, place approximately 2 μl of Fluoromount G quench, then immediately transfer approximately 1 μl of DFA reaction tube and mix well with pipet tip. Note: the quench to reaction tube ratio should be 2:1; adjust volumes accordingly. Transfer approximately 2 μl of the quench/DFA reaction material to microscope slide and add cover slip.

Repeat steps for each test and control sample one at a time as the Fluoromount G will solidify rather quickly.

Examine cells using epifluorescent microscopy equipped with appropriate filters (EF-4 TEXAS RED (sulforhodomine 101 acid chloride) HyQ or equivalent for viewing Dylight 594 conjugated anti-pCHO FAb; B-2E/C or equivalent for FITC conjugated anti-capsule IgM).

Individual cell(s) are examined for both epifluorescent signals simultaneously via switching of filters. Cell(s) positive for capsule will appear brilliant green; positively stained *B. anthracis* pCHO of vegetative cells will emit bright red either along periphery of vegetative cells or just at septa; negative pCHO staining will result in 'shadow' effect. A positive pXO2$^+$ *B. anthracis* should stain for both antigens whereas a pXO2$^-$ strain (i.e. *B. anthracis* Sterne) will only stain for the pCHO (FIG. 2).

Confirm that the stained cells are intact by examination via bright field. Vegetative cells that appear 'empty' indicate cell death and cell wall integrity compromised thus allowing antibody to possibly enter and become 'trapped'. Vegetative cells should appear opaque under bright field examination.

Repeat the DFA assay up to 3 hours if the capsule DFA results are questionable. Failure of capsule production at 3 hours for the *B. anthracis* Pasteur control indicates a failure within the assay and the entire assay should be repeated with freshly prepared cultures. Although a poor capsule producer, presence of capsule on the Pasteur strain either in punctuate or entire form along with the staining of the secondary cell wall pCHO indicates successful culturing and staining via the tandem antibody(s); negative results exhibited by sample should be rendered accurate.

NOTE: Incubation of cultures over 3 hours may introduce extraneous proteins that could interfere with the pCHO antibody binding. Historically, the whole anti-pCHO IgM molecule was used for staining the vegetative cells of anthracis. This form also did not stain 100% of vegetative cells within a given sample. The question of why was not answered until the development of the tandem DFA assay. Optimizing the assay revealed issues regarding the deposition of EA1 and/or SAP proteins during late lag/early log phase which masked the galactose-N-acetyl-glucosamine (pCHO) motif presented on the cell wall of *anthracis*. In order to utilize the pCHO FAb as intended in tandem with the capsule MAb, it was necessary to optimize not only the time and growth conditions for capsule production, but also the pre-EA1/SAP deposition. This "window" has fallen into a 2-3 hour range.

In addition, the negative and positive controls for the tandem DFA assay have to be in the same form as the test sample, i.e. the vegetative cells form. This is because, for example, if spores were used for the positive control vs. vegetative cells as the test sample, the production of capsule would perhaps be skewed towards the spores; this would not be an absolute comparison for the vegetative cell form sample. Therefore, it is best to confirm that the culture conditions are correct for the positive control to produce capsule; a poor capsule producer is used here in order to have confidence that if the control is able to produce capsule, then the conditions were optimized for the test sample to also produce capsule. The positive control should not be presented in spore form for it will easily produce capsule and the likelihood of the submitted sample being in spore form is low.

What is claimed is:

1. A method for detecting the presence of *Bacillus anthracis* in a sample, said method comprising
   (i) culturing for 2-3 hours a single sample under conditions suitable to induce formation of *Bacillus anthracis* capsule, and thereby producing a single cultured sample;

(ii) directly following step (i), contacting said single cultured sample in a single container means with two antibodies in tandem, antibodies one and Fab antibody two, each detectably labeled with a different identifiable signal moiety, such that said two antibodies are present in the same culture sample together in said single container means, wherein antibody one specifically binds to a capsule antigen, and Fab antibody two has a radius sufficiently small so as to permeate the *Bacillus anthracis* capsule, and Fab antibody two specifically binds to a cell wall antigen, and binds to the cell wall antigen even in the presence of capsule-inducing conditions; and (iii) detecting the presence of the detectable signal from antibody one and Fab antibody two wherein the presence of detectable signal from both antibodies indicates presence of *Bacillus anthracis* in said single cultured sample.

2. The method of claim 1, wherein antibody one specifically binds to *Bacillus anthracis* capsule poly-D-glutamic acid.

3. The method of claim 2, wherein antibody one is mAb FDF-1B9.

4. The method of claim 1 wherein Fab antibody two specifically binds to *Bacillus anthracis* cell wall galactose-N-acetyl-glucosamine.

5. The method of claim 4 wherein said Fab antibody two is mAb EAII-6G6 Fab.

6. The method of claim 3 wherein said Fab antibody two is mAb EAII-6G6 Fab.

7. The method of claim 1 wherein antibody one and Fab antibody two are labeled with a contrasting fluorophore.

8. The method of claim 7 wherein the fluorophore is fluorescein isothiocyanate, rhodamine, luciferin, auramine, sulforhodamine 101 acid chloride, carboxamido-(6-azido-hexanyl), triethyammonium salt, or AMCA blue.

9. The method of claim 1, wherein the sample is a forensic sample.

10. The method of claim 1 wherein said sample is a biological sample obtained from a subject, which biological sample includes one or more of cells, blood, tissues, or biological fluid.

11. The method of claim 1, wherein the sample is selected from the group consisting of soil, water, or food product.

12. The method of claim 1, wherein the Fab antibody two has a Stokes radius 4.6 nm or less.

13. The method of claim 1, wherein the Fab antibody two has a Stokes radius 3.2 nm or less.

14. A method for detecting the presence of *Bacillus anthracis* in a single sample, without first culturing the sample, said method comprising (i) contacting a single sample with two antibodies in tandem in a single container means, antibodies one and Fab antibody two, each detectably labeled with a different identifiable signal moiety wherein cells in the sample are intact and in vegetative form, uncultured, and less than 24 hours old, antibody one specifically binds to a capsule antigen, and Fab antibody two has a radius sufficiently small so as to permeate the *Bacillus anthracis* capsule, and Fab antibody two specifically binds to a cell wall antigen, and binds to the cell wall antigen even in the presence of capsule-inducing conditions; and (ii) detecting the presence of the detectable signal from antibody one and Fab antibody two wherein the presence of detectable signal from both antibodies indicates presence of *Bacillus anthracis* in said single sample.

15. The method of claim 14, which comprises the further steps for confirming the results of step (ii) by (iii) incubating the sample for 2-3 hours, under conditions suitable to induce formation of *Bacillus anthracis* capsule, thereby producing a single cultured sample, (iv) directly following step (iii), contacting said single cultured sample in said single container means with two antibodies in tandem, antibodies one and Fab antibody two, each detectably labeled with a different identifiable signal moiety wherein antibody one specifically binds to a capsule antigen, and Fab antibody two has a radius sufficiently small so as to permeate the *Bacillus anthracis* capsule, and Fab antibody two specifically binds to a cell wall antigen, and binds to the cell wall antigen even in the presence of capsule-inducing conditions; and (v) detecting the presence of the detectable signal from antibody one and Fab antibody two wherein the presence of detectable signal from both antibodies indicates presence of *Bacillus anthracis* in said single cultured sample.

16. The method of claim 14, wherein antibody one specifically binds to *Bacillus anthracis* capsule poly-D-glutamic acid, and wherein Fab antibody two specifically binds to *Bacillus anthracis* cell wall galactose-N-acetyl-glucosamine.

* * * * *